United States Patent
White et al.

(10) Patent No.: US 9,020,538 B1
(45) Date of Patent: Apr. 28, 2015

(54) SYSTEM AND METHOD FOR DISPLAYING SURF INFORMATION TO A USER

(71) Applicant: Nixon, Inc., Encinitas, CA (US)

(72) Inventors: Tyson White, Encinitas, CA (US); Joe Babcock, Encinitas, CA (US); Nick Everist, Encinitas, CA (US)

(73) Assignee: Nixon, Inc., Encinitas, CA (US)

( * ) Notice: Subject to any disclaimer, the term of this patent is extended or adjusted under 35 U.S.C. 154(b) by 0 days.

(21) Appl. No.: 14/468,280

(22) Filed: Aug. 25, 2014

Related U.S. Application Data (60) Provisional application No. 62/038,829, filed on Aug. 18, 2014.

(51) Int. Cl.
| | |
|---|---|
| H04W 4/02 | (2009.01) |
| H04W 64/00 | (2009.01) |
| G01S 19/19 | (2010.01) |
| G04G 9/00 | (2006.01) |

(52) U.S. Cl.
CPC ............... *H04W 4/02* (2013.01); *H04W 64/00* (2013.01); *G01S 19/19* (2013.01); *G04G 9/0064* (2013.01)

(58) Field of Classification Search
CPC ..... G04G 9/0064; G04G 99/006; G01S 19/19
USPC ............... 455/414.1, 456.1, 456.3, 566, 418
See application file for complete search history.

(56) References Cited

U.S. PATENT DOCUMENTS

| | | | |
|---|---|---|---|
| 2014/0113613 A1* | 4/2014 | Huang et al. | 455/418 |
| 2014/0176426 A1* | 6/2014 | Morohoshi | 345/156 |

OTHER PUBLICATIONS http://www.nixon.com/us/en/nxn/nixon-surf-watches?gclid=CJ3j5K652cACFURgfgod9L0, Sep. 11, 2014, 3 pages.
http://searchgps.ripcurl.com/welcome/the-app.php, Sep. 11, 2014, 3 pages.
http://searchgps.ripcurl.com/welcome/the-watch.php, Sep. 11, 2014, 3 pages.
http://searchgps.ripcurl.com/welcome, Sep. 11, 2014, 3 pages.
http://www.mypebblefaces.com/apps/11061/7279; Sep. 11, 2014, 5 pages.
http://pebble.challengepost.com/submissions/21553-watch-surf-the-world-s-first-surf-watch, Sep. 11, 2014, 4 pages.
http://www.ripcurl.com/searchgps-1.html, Sep. 11, 2014, 4 pages.

* cited by examiner

*Primary Examiner* — Barry Taylor
(74) *Attorney, Agent, or Firm* — Pillsbury Winthrop Shaw Pittman LLP (57) ABSTRACT

This disclosure relates to a system configured to display current surf information to a user on a device worn by the user, track physical surfing activity of the user across multiple surf sessions, and/or alert the user when current surf conditions match previously highly rated surf conditions and/or any user selected criteria based on surf/weather forecast data. The system may comprise a first device (a watch) worn by the user, a second device (the user's smartphone) associated with the user but physically separate and unconnected from the first device, external resources, and/or other components.

9 Claims, 10 Drawing Sheets

SYSTEM AND METHOD FOR DISPLAYING SURF INFORMATION TO A USER

FIELD OF THE DISCLOSURE

This disclosure relates to a system and method for displaying surf information to a user via a user interface carried by a device worn by the user.

BACKGROUND

Waterproof watches that display tide chart information to users are known. Typically, the tide chart information displayed to users on such watches is predictive tide information determined days, weeks, months, or even years in advance. The watches simply regurgitate this predetermined information and do not provide any information freshly gathered from output signals of oceanic and/or other environmental sensors.

SUMMARY

One aspect of the disclosure relates to a method for displaying surf information to a user via a user interface carried by a first device worn by the user. The method comprises obtaining information related to a desired physical, geographic surf location of the user with a second device, the second device being physically separate and unconnected from the first device, and being associated with the user; obtaining, with the second device, surf information for the desired surf location of the user, wherein the surf information for the desired surf location may be regularly obtained from one or more external sources of information accessed via a wireless communication network such that the obtained surf information reflects substantially current surf information for the desired surf location of the user; wirelessly communicating the obtained surf information to the first device responsive to the first device being in proximity to the second device to facilitate communication between the first device and the second device; and displaying the communicated surf information to the user via the user interface carried by the first device.

Another aspect of the disclosure relates to a system configured to display surf information to a user. The system comprises a device worn by the user that carries a user interface configured to display surf information to the user. The surf information may be received from one or more physical computer processors configured by computer readable instructions to: obtain information related to a desired physical, geographic surf location of the user wearing the device; obtain surf information for the desired surf location of the user, wherein the surf information for the desired surf location may be regularly obtained from one or more external sources of information accessed via a wireless communication network such that the obtained surf information reflects substantially current surf information for the desired surf location of the user; communicate the obtained surf information to the device worn by the user; and cause the device worn by the user to display the communicated surf information to the user via the user interface.

A third aspect of the disclosure relates to a system configured to provide surf information to a user via an electronic application configured to receive surf information from one or more remote server computers and communicate the surf information to a device worn by the user for display to the user. The system comprises one or more physical computer processors configured by computer readable instructions to: obtain information related to a desired physical, geographic surf location of the user; regularly obtain surf information for the desired surf location of the user from the one or more remote server computers accessed via a wireless communication network such that the obtained surf information reflects substantially current surf information for the desired surf location of the user; communicate the obtained surf information to the device worn by the user; and cause a user interface carried by the device worn by the user to display the communicated surf information to the user.

A fourth aspect of the disclosure relates to a system configured to track physical surfing activity of a user. The system comprises a first device worn by the user configured to generate and store information related to physical surfing activity of a user during a current surf session. The first device comprises one or more sensors, electronic storage, and/or other components. The one or more sensors may be configured to generate output signals conveying information related to the physical surfing activity of the user during the current surf session. The electronic storage may be configured to electronically store the information related to the physical surfing activity of the user during the current surf session. The first device may be configured to communicate with a second device associated with the user that is physically separate and unconnected from the first device. The second device may comprise one or more physical computer processors configured to: responsive to the user completing the current surf session, obtain the information related to the physical surfing activity of the user during the current surf session; determine one or more current surf parameters for the current surf session, the current surf parameters indicating an amount of physical surfing activity of the user during the current surf session; and electronically store the current surf parameters with corresponding previous surf parameters determined for previous surf sessions to facilitate tracking the user's individual surfing activity for multiple surf sessions.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
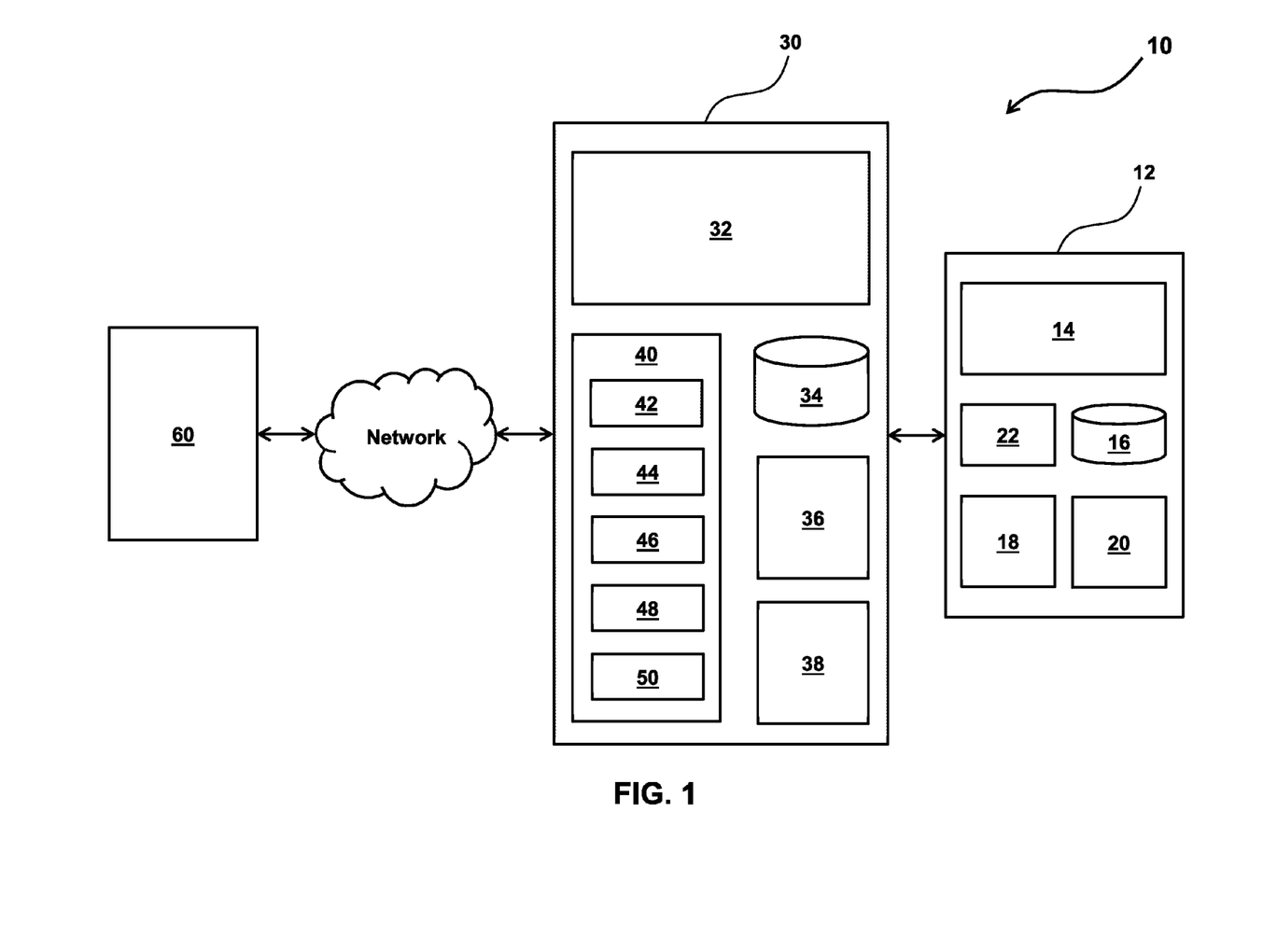
FIG. 1 illustrates a system configured to display current surf information to a user on a device worn by the user, track physical surfing activity of the user across multiple surf sessions, alert the user when current surf conditions match previously highly rated surf conditions and/or any user selected criteria based on surf/weather forecast data, and/or perform other actions.

FIG. 1 illustrates a system 10 configured to display current surf information to a user on a device worn by the user, track physical surfing activity of the user across multiple surf sessions, alert the user when current surf conditions match previously highly rated surf conditions and/or any user selected criteria based on surf/weather forecast data, and/or perform other actions. System 10 may comprise a first device 12 worn by the user, a second device 30 associated with the user but physically separate and unconnected from first device 12, external resources 60, and/or other components. In some implementations, first device 12 may be a watch worn by the user and second device 30 may be the user's smartphone, for example.

Current surf information may include recent information received, stored, transmitted, etc. by external sources of information (e.g., external resources 60 such as sensors, server computers, and/or other external resources as described herein) and then obtained by system 10, information determined by system 10 (e.g., a surf session duration, a surf session rating, a surf session location, a surf session wave count, etc.), and/or other information. Current surf information may include real-time and/or near real time information related to physical observable conditions, forecasts, ratings, reports, and/or other information. For example, current surf information may include information received by a server from an oceanic sensor that reflects current oceanic conditions (e.g., real world observable conditions) conveyed by the sensor output signals (e.g., as opposed to months old pre-determined tide chart data). Current surf information may include information such as the date, the time, the name of a surf break for which information is obtained, a current wave height, a current surf condition rating, a current tide indication, a current water temperature, an alert indicator (e.g., a high surf advisory, a surf conditions ratings based alert, etc.), a tide graph with an indication of the current tide level, a current air temperature, a surf forecast, current weather information, a surf session duration, a surf session rating, a surf session wave count, surf session physical activity tracking information (e.g., wave count, session duration, paddle count, etc.), sunrise/sunset information, and/or other surf information. In some implementations, current surf information may include forecasted and/or past surf conditions. For example, system 10 may be configured to display future forecasted data, and/or past data in some instances.

Figure 2:
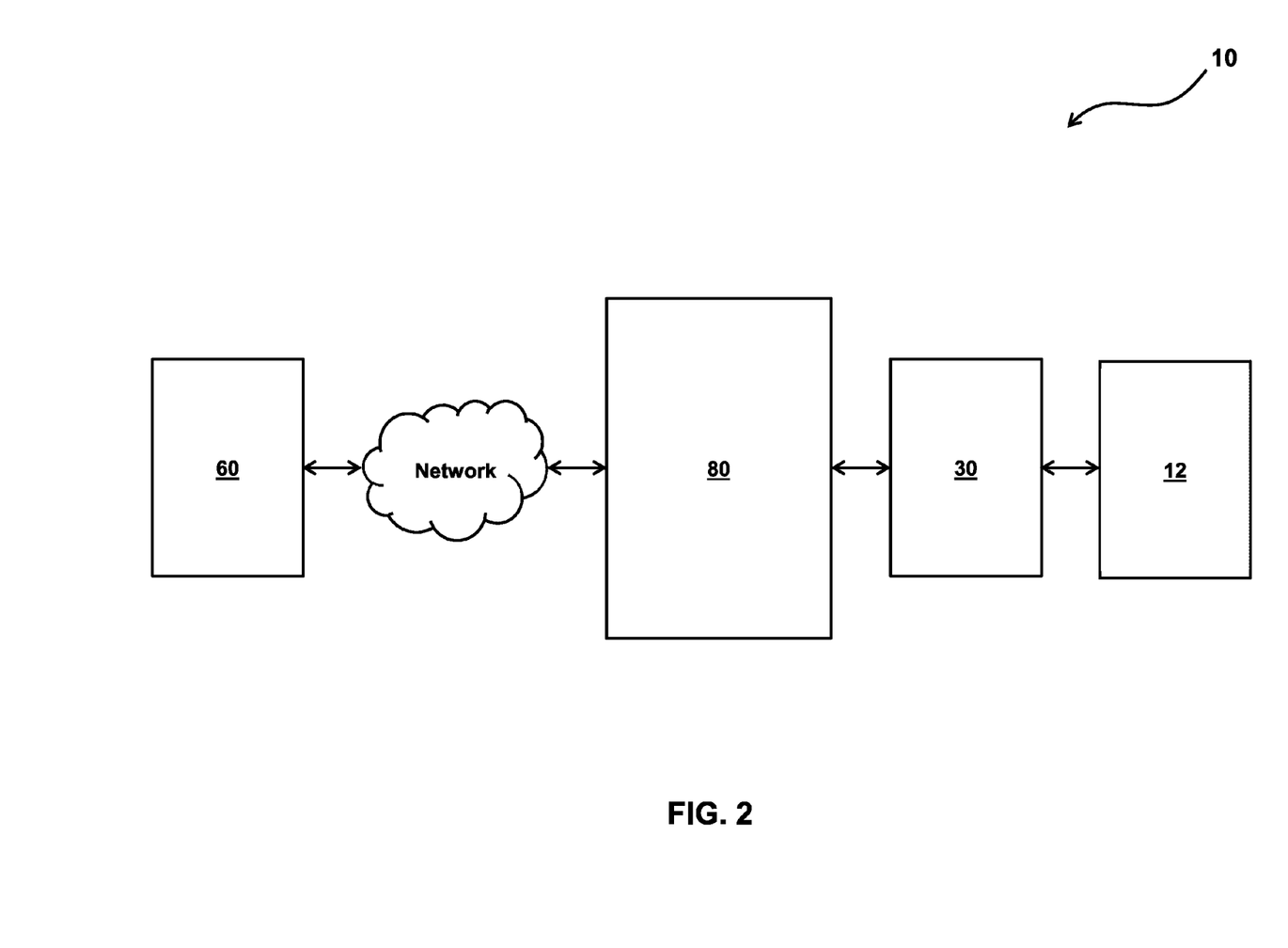
FIG. 2 illustrates another possible implementation of the system.

As shown in FIG. 1, system 10 may be configured such that a user's smartphone (e.g., second device 30) runs an electronic application (e.g., an "app", the functionality of which is described herein related to a processor 40 of second device 30) that obtains at least some of the current surf information from external resources 60 and then communicates it to a watch worn by a user (e.g., first device 12) for display to the user. In some implementations, as shown in FIG. 2, system 10 may be configured such that the electronic application run by the user's smartphone (second device 30) receives at least some of the current surf information from a server 80 associated with system 10. Server 80 may collect, gather, determine, and/or otherwise obtain the current surf information from external resources 60. For example, server 80 may obtain current surf information via an external server that is part of external resources 60. The external server may provide an application programming interface (API) for server 80 to facilitate communication of the current surf information between the servers. In some implementations, communication to first device 12 may be direct from external resources, such as the API and/or other external resources 60, by wireless methods such as Bluetooth Low Energy and/or other wireless protocols, and/or wired (e.g., hard wired) connections, and/or may be transmitted to first device 12 via other external resources after being processed and/or modified by other external resources such as a smartphone, a smartphone app, and/or other resources.

Returning to FIG. 1, presenting current surf information to a user on a watch (e.g., first device 12) worn by a user may include effectuating presentation of a graphical user interface. The graphical user interface may include one or more views that include one or more fields configured to display the different types of surf information to the user. FIG. 3A-FIG. 3E illustrate various views of the graphical user interface presented to the user on a watch worn by the user. FIG. 3A-FIG. 3E are non-limiting examples of possible views of the graphical user interface. Various views of the graphical interface may include and/or exclude any and/or all of the fields shown in FIG. 3A-FIG. 3E, and/or additional fields not shown in the figures. The views may include any number and/or any types of fields and they may be presented in any way that allows system 10 to function as described herein.

Figure 3A:
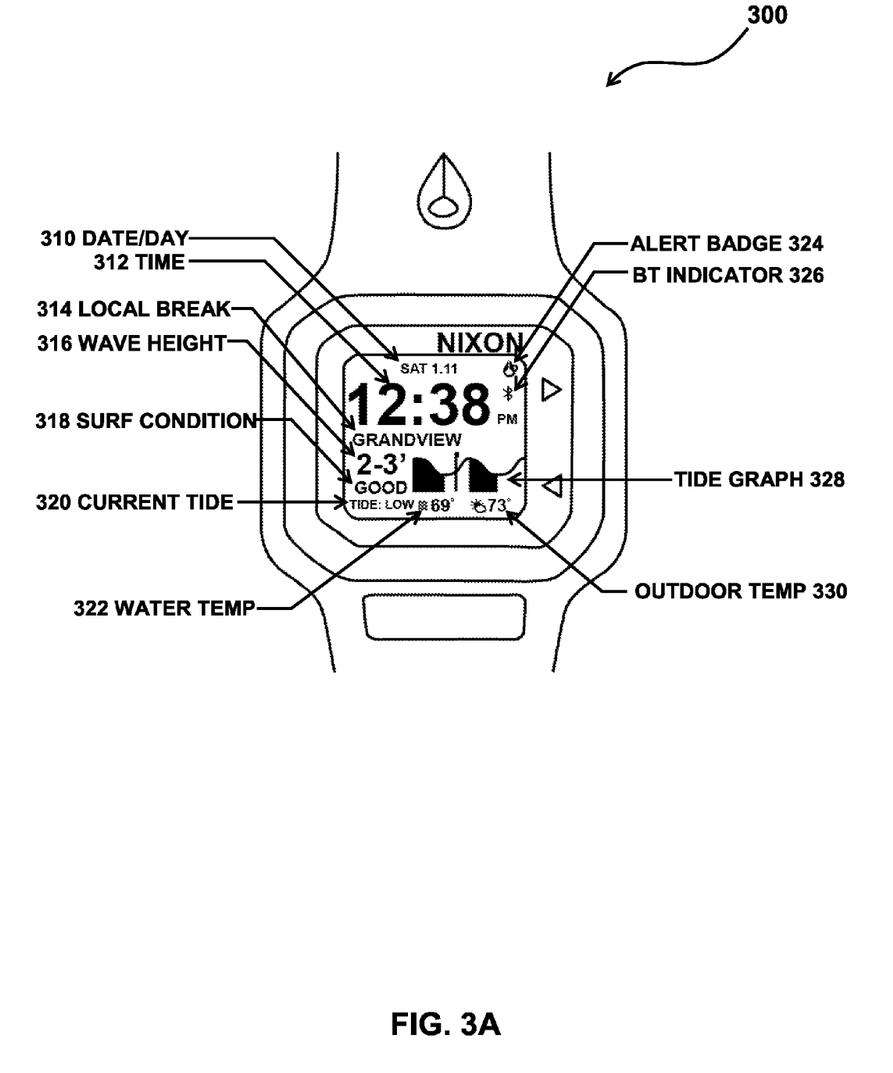
FIG. 3A illustrates a first example of a possible view of the graphical user interface presented to the user on a watch worn by the user.

FIG. 3A illustrates a first example of a possible view 300 of the graphical user interface presented to the user on a watch worn by the user. FIG. 3A illustrates a date/day field 310, a time field 312, a local break field 314, a wave height field 316, a surf condition field 318, a current tide field 320, a water temp field 322, an alert badge field 324, a Bluetooth indicator field 326 (Bluetooth connectivity described in more detail below), a tide graph field 328, and an outdoor temp field 330.

Figure 3B:
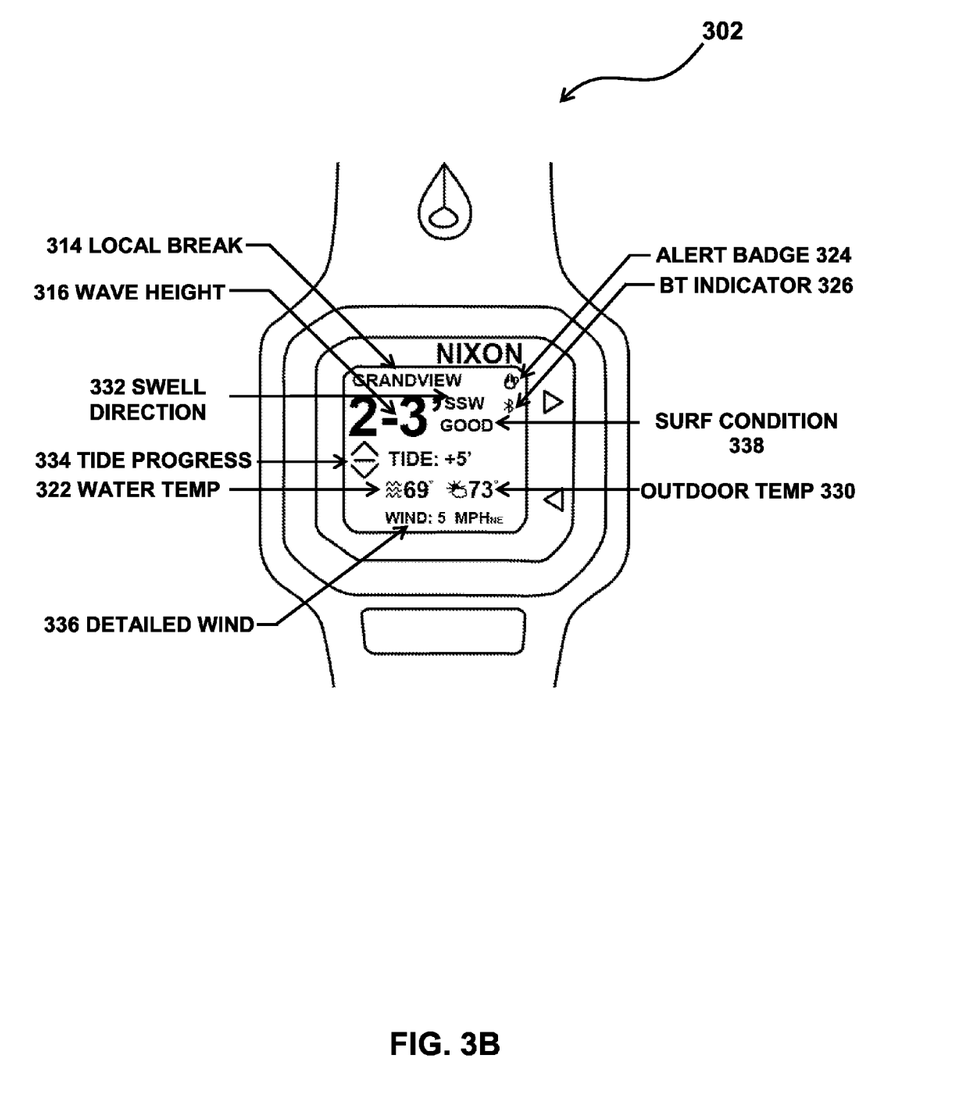
FIG. 3B illustrates a second example of a possible view of the graphical user interface presented to the user on a watch worn by the user.

FIG. 3B illustrates a second example of a possible view 302 of the graphical user interface presented to the user on a watch worn by the user. FIG. 3B illustrates local break field 314, wave height filed 316, a swell direction field 332, a tide progress field 334, water temp field 322, a detailed wind field 336, alert badge field 324, Bluetooth indicator field 326, a surf condition field 338, and outdoor temperature field 330.

Figure 3C:
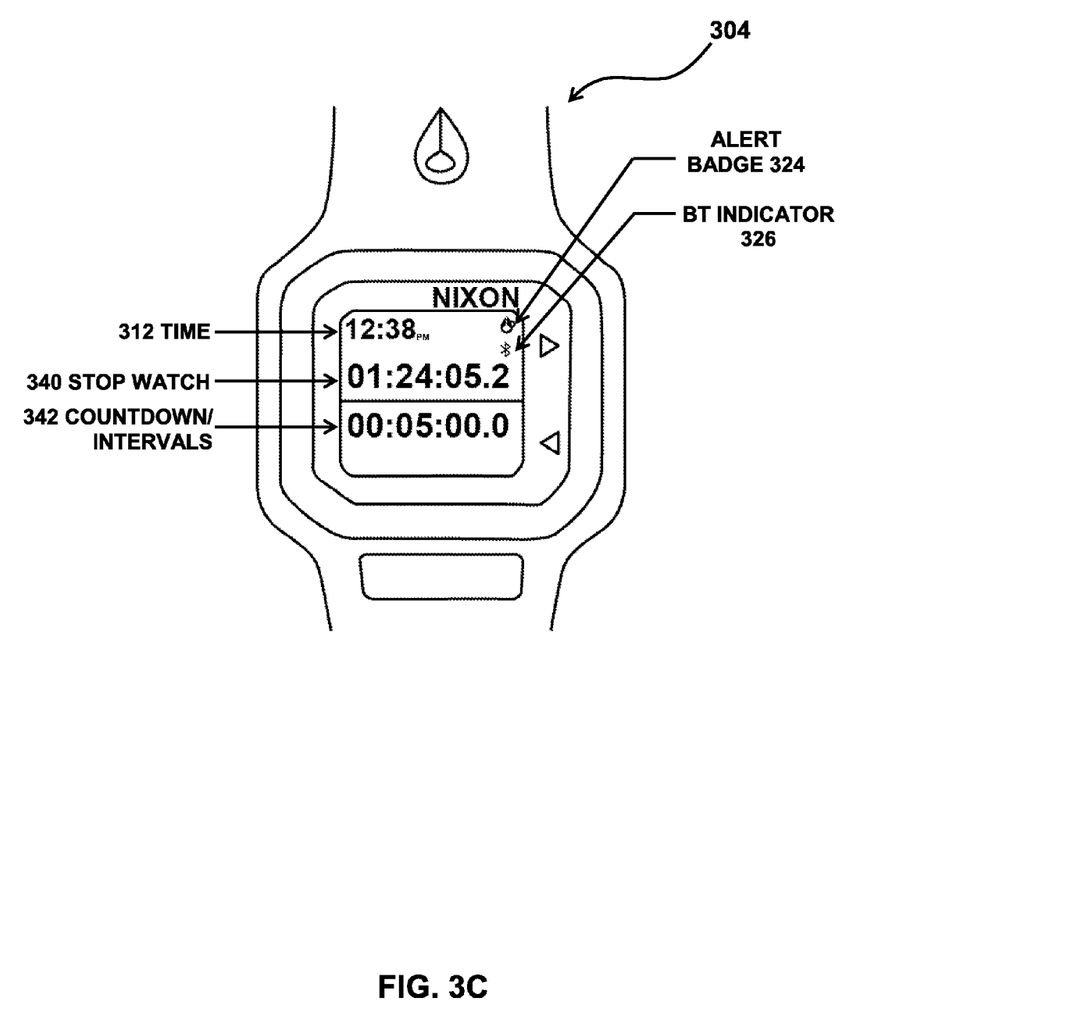
FIG. 3C illustrates a third example of a possible view of the graphical user interface presented to the user on a watch worn by the user.

FIG. 3C illustrates a third example of a possible view 304 of the graphical user interface presented to the user on a watch worn by the user. FIG. 3C illustrates time field 312, a stop watch field 340, a countdown/intervals field 342, alert badge field 324, and Bluetooth indicator field 326.

Figure 3D:
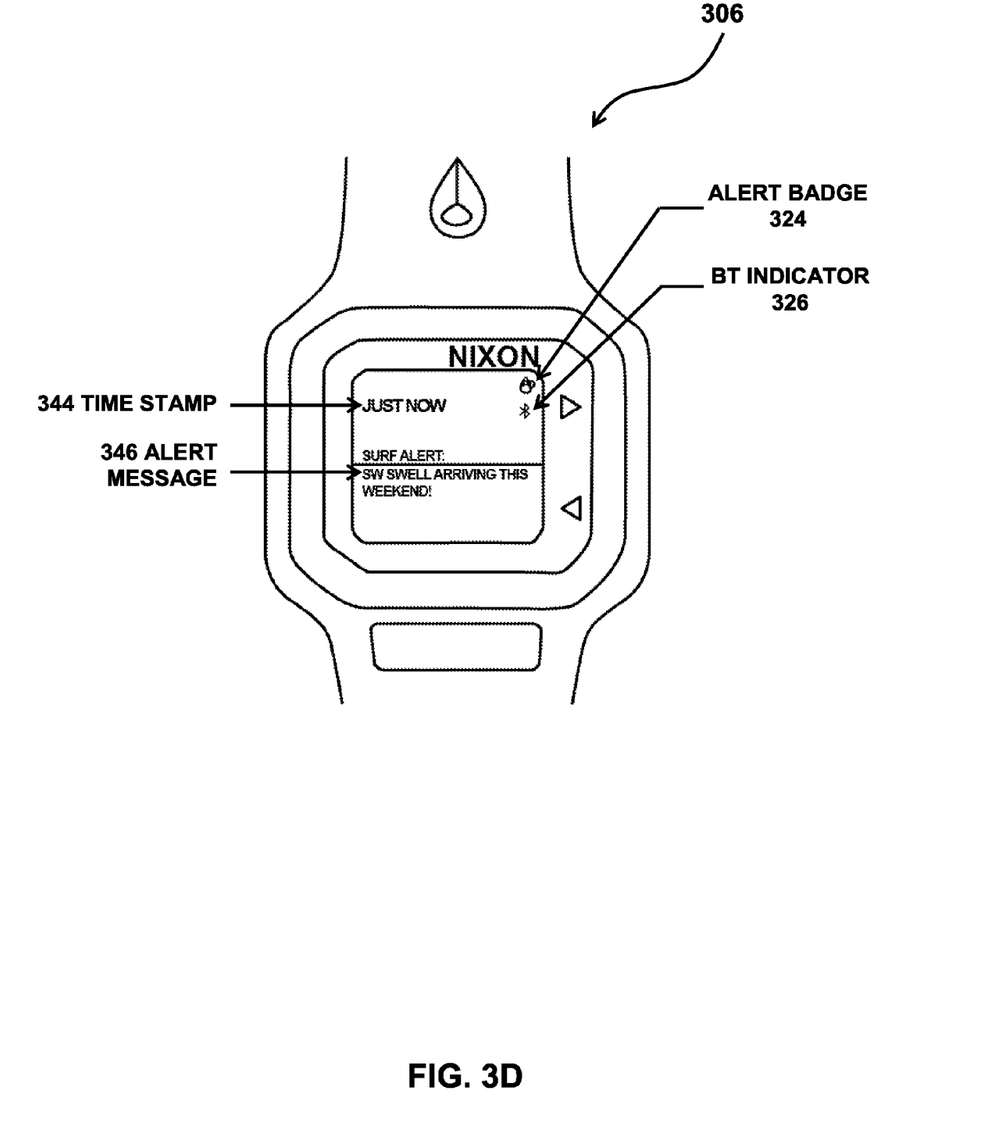
FIG. 3D illustrates a fourth example of a possible view of the graphical user interface presented to the user on a watch worn by the user.

FIG. 3D illustrates a fourth example of a possible view 306 of the graphical user interface presented to the user on a watch worn by the user. FIG. 3D illustrates a time stamp field 344, an alert message field 346, alert badge field 324, and Bluetooth indicator field 326.

Figure 3E:
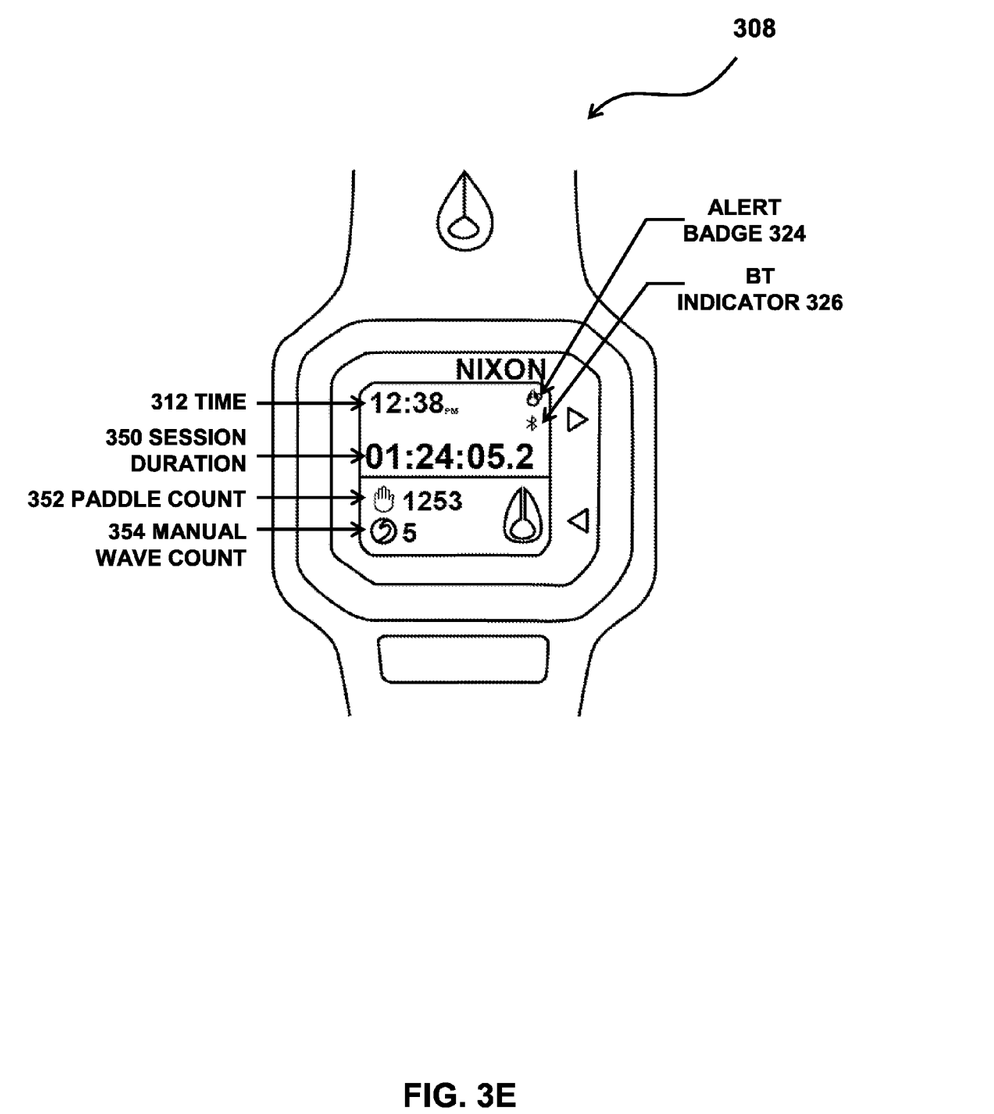
FIG. 3E illustrates a fifth example of a possible view of the graphical user interface presented to the user on a watch worn by the user.

FIG. 3E illustrates a fifth example of a possible view 308 of the graphical user interface presented to the user on a watch worn by the user. FIG. 3E illustrates time field 312, a session duration field 350, a paddle count field 352, a manual wave count field 354, alert badge field 324, and Bluetooth indicator field 326. As described above, the views and/or fields illustrated in FIG. 3A-FIG. 3E are not intended to be limiting. The possible views of the graphical user interface presented to the user on a watch worn by the user may include any number of views and/or any number and/or types of fields that present current surf information and/or other information to the user.

Returning to FIG. 1, as described above, first device 12 may be configured to be worn by the user and display surf information to a user via a user interface 14 carried by first device 12. First device 12 may be configured to be light weight and small enough to be comfortably worn by the user. In some implementations, first device 12 may be configured to be comfortably worn by the user while the user goes surfing. In some implementations, first device 12 may be a watch. In some implementations, the watch may be waterproof and/or water resistant. First device 12 may comprise one or more of user interface 14, electronic storage 16, a processor 18, communications components 20, sensors 22, and/or other components.

User interface 14 may be configured to provide an interface between first device 12 and a user through which the user may provide information to and receive information from system 10. This enables data, cues, results, and/or instructions and any other communicable items, collectively referred to as "information," to be communicated between the user and system 10. By way of a non-limiting example, user interface 14 may be configured to display the current surf information (e.g., including forecasted and/or past surf conditions if appropriate) to the user. As described above, displaying current surf information may include effectuating presentation of the graphical user interface which may include one or more views that include one or more fields configured to display the different types of surf information to the user (e.g., FIG. 3A-FIG. 3E). For example, the one or more fields may display one or more of the date, the time, the surf break name, the wave height, the surf condition rating, the current tide indication, the water temperature, the alert indicator, the tide graph, the air temperature, the surf forecast, the weather information, a Bluetooth connectivity indicator, surf session physical activity tracking information (e.g., wave count, session duration, paddle count, etc.), sunrise/sunset information, and/or other surf information. In some implementations, user interface 14 may be configured to display substantially all of the surf information and/or a subset of related surf information (e.g., as illustrated in FIG. 3A-FIG. 3E) to the user in a single view (which may be more convenient for the user than having to navigate through multiple views to view the information). Examples of interface devices suitable for inclusion in user interface 14 may include a display, a touch screen display, touch sensitive and/or physical buttons, and/or other interface devices.

Processor 18 may be configured to provide information processing capabilities in first device 12. As such, processor 18 may comprise one or more of a digital processor, an analog processor, a digital circuit designed to process information, an analog circuit designed to process information, a state machine, and/or other mechanisms for electronically processing information. Processor 18 may be configured to provide at least some of the functionality attributed herein to first device 12. For example, processor 18 may facilitate electronic storage of information conveyed by output signals from sensors 22 included in first device 12 (described below).

Communication components 20 may be configured to facilitate communication between first device 12 and second device 30 and/or other devices. Communication components 20 may facilitate wireless and/or wired communication. For example, communication components 20 may facilitate wireless communication via a Wi-Fi network, via Bluetooth technology, the internet, a cellular network, and/or other wireless technology. In some implementations, communication components 20 may facilitate communication via a wired USB connection, for example.

Sensors 22 may be configured to generate output signals conveying information related to the physical surfing activity of the user during a current surf session, a physical geographic location of a user, environmental conditions, and/or other information. In some implementations, sensors 22 may include one or more of a GPS sensor, a gyroscope, an accelerometer, an altimeter, a temperature sensor, a barometer, an anemometer, a magnetometer, a compass, a heart rate monitor, an ambient light sensor, and/or other sensors. The physical surfing activity of the user during the current surf session may refer to activities such as riding waves, paddling, kicking, resting, aerial maneuvers, crashes, diving and/or being forced down at depth below water, generating g-forces, and/or other activities.

Electronic storage 16 may comprise electronic storage media that electronically stores information. Electronic storage 34 may store software algorithms; information obtained, received, and/or determined by processor 40 (described below), processor 18, external resources 60, and/or other devices; information obtained, received, and/or determined via sensors 22, sensors 36 (described below), and/or other sensors; and/or other information that enables system 10 to function as described herein. For example, electronic storage 16 may be configured to electronically store the information related to the physical surfing activity of the user during the current surf session (e.g., information conveyed by the output signals of sensors 22).

As describe above, second device 30 may be associated with the user but physically separate and unconnected from first device 12. In some implementations, second device 30 may be the user's smartphone, for example. Second device 30 may comprise one or more of a user interface 32, electronic storage 34, a sensor 36, communications components 38, a processor 40, and/or other components.

User interface 32 may be configured to provide an interface between second device 30 and a user through which the user may provide information to and receive information from system 10. This enables data, cues, results, and/or instructions and any other communicable items, collectively referred to as "information," to be communicated between the user and system 10. By way of a non-limiting example, user interface 32 may be configured to receive information indicating a desired surf location, a surf session rating after surfing that indicates enjoyment level of the user for the current surf session, and/or other information. Receiving entry and/or selection of a desired surf location, a surf session rating, and/or other information may include a user typing information via a key pad, a keyboard, and/or a touch screen; selecting (e.g., via a touchscreen) information from a list of choices provided to the user, making a selection via slider icon displayed by user interface 32, and/or other entry and/or selection. Examples of interface devices suitable for inclusion in user interface 32 include a touch screen, a keypad, touch sensitive and/or physical buttons, switches, a keyboard, knobs, levers, speakers, a microphone, an indicator light, a printer, and/or other interface devices.

It is to be understood that other communication techniques, either hard-wired or wireless, are also contemplated by the present disclosure as user interface 32. For example, the present disclosure contemplates that user interface 32 may be integrated with a removable storage interface provided by electronic storage 34. In this example, information may be loaded into system 10 from removable storage (e.g., a smart card, a flash drive, a removable disk) that enables the user to customize the implementation of system 10. Other exemplary input devices and techniques adapted for use with system 10 as user interface 32 include, but are not limited to, an RS-232 port, RF link, an IR link, modem (telephone, cable or other). In short, any technique for communicating information with system 10 is contemplated by the present disclosure as user interface 32.

Figure 4:
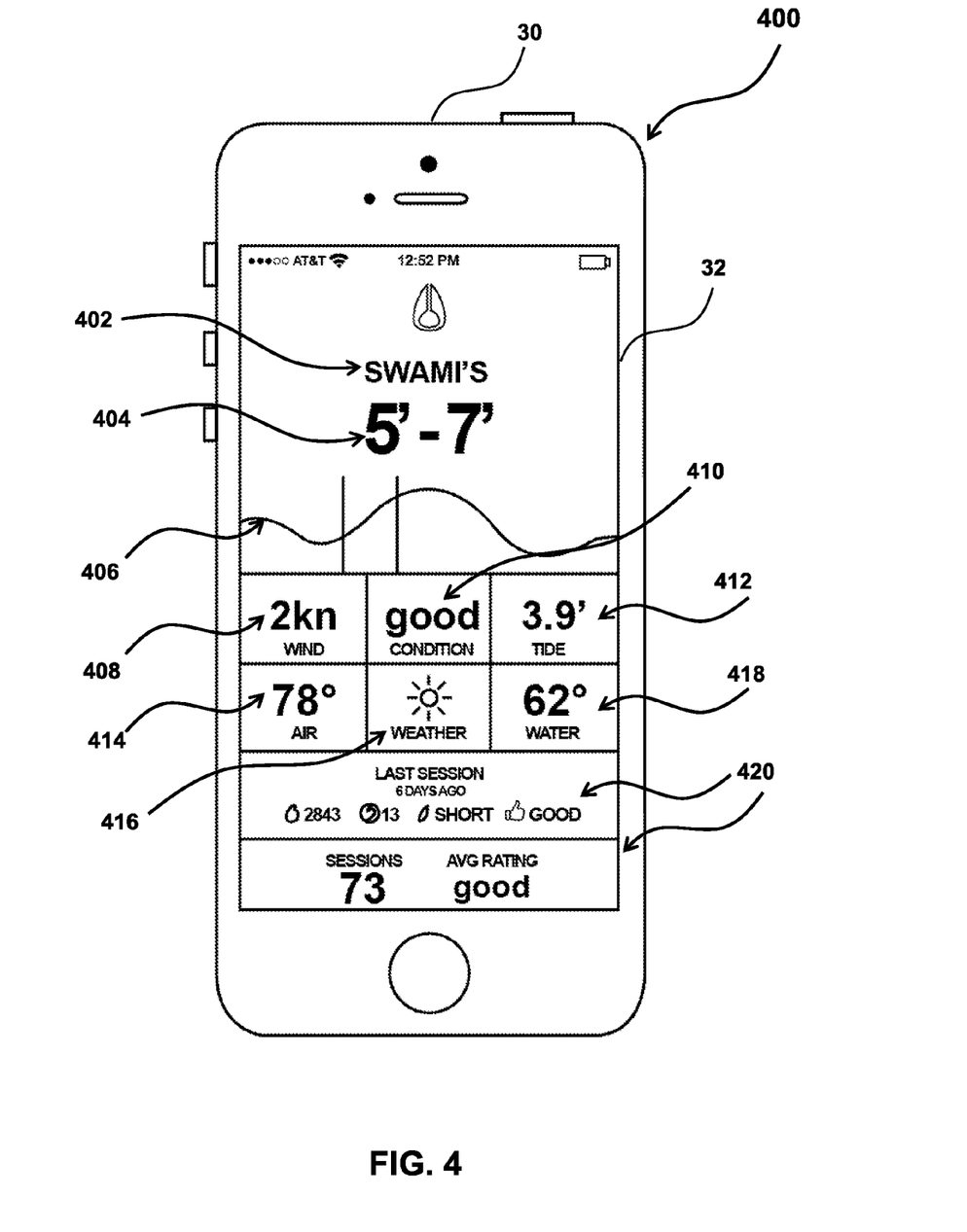
FIG. 4 illustrates a possible example of a view of a user interface presented to the user on the user's smartphone.

FIG. 4 illustrates a possible example of a view 400 of user interface 32 of second device 30 (the user's smartphone). View 400 presents information such as break name 402, wave height 404, tide information 406, wind information 408, a surf conditions rating 410, a current tide level 412, current air temperature 414, weather information 416, a current water temperature 418, and information related to one or more previous surf sessions 420. View 400 is not intended to be limiting. User interface 32 may present any information to the user and/or receive any information from the user (e.g., location information described above, surf session rating information described below, etc.) that allows system 10 to function as described herein.

Returning to FIG. 1, electronic storage 34 may comprise electronic storage media that electronically stores information. The electronic storage media of electronic storage 34 may comprise one or both of system storage that is provided integrally (i.e., substantially non-removable) with second device 30 and/or removable storage that is removably connectable to second device 30 via, for example, a port (e.g., a USB port, a firewire port, etc.) or a drive (e.g., a disk drive, etc.). Electronic storage 34 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 34 may store software algorithms; information (e.g., surf information) obtained, received, and/or determined by processor 40, processor 18, and/or external resources 60; and/or other information that enables system 10 to function as described herein.

Sensors 36 are configured to generate output signals conveying information related to a physical geographic location of second device 30, proximity of first device 12 to second device 30, presence of saved surf sessions that are ready to be synced, general watch setup, timer set, alarm set, time/date set, battery level, general status, and/or other information. By way of a non-limiting example, sensors 36 may include one or more of a GPS location sensor, a signal strength sensor for detecting proximity of first device 12, and/or other sensors. The output signals from sensors 36 may be used by processor 40 for obtaining and/or determining a desired surf location of the user, determining proximity of first device 12 to facilitate tracking a user's surfing activity during the current surf session, and/or for other purposes.

Communication components 38 may be configured to facilitate communication between first device 12 and second device 30, between second device 30 and external resources 60, and/or between other devices. Communication components 38 may facilitate wireless and/or wired communication. For example, communication components 38 may facilitate wireless communication via a Wi-Fi network and/or via Bluetooth technology with first device 12; and via the internet, a cellular network, and/or other wireless technology with external resources 60. In some implementations, communication components 38 may facilitate communication via a wired USB connection with first device 12, for example.

Processor 40 may be configured to provide information processing capabilities in second device 30 individually, and/or system 10 as a whole. As such, processor 40 may comprise one or more of a digital processor, an analog processor, a digital circuit designed to process information, an analog circuit designed to process information, a state machine, and/or other mechanisms for electronically processing information. Although processor 40 is shown in FIG. 1 as a single entity within second device 30, this is for illustrative purposes only. In some implementations, processor 40 may comprise a plurality of processing units. These processing units may be physically located within the same device (e.g., within a server that is part of external resources 60, within a smartphone such as second device 30, within a watch such as first device 12, within a desktop computer, within a laptop computer, within a tablet computer, and/or other computing devices), or processor 40 may represent processing functionality of a plurality of devices operating in coordination (e.g., a server that is part of external resources 60, a smartphone such as second device 30, a watch such as first device 12).

Processor 40 may be configured to execute computer program components. The computer program components may be configured to enable an expert and/or user to interface with second device 30 and/or system 10 and/or provide other functionality attributed herein to first device 12, second device 30, external resources 60, and/or other components of system 10. The computer program components may include a location component 42, a surf information component 44, a communication component 46, a display component 48, an activity tracking component 50, and/or other components. Processor 40 may be configured to execute components 42, 44, 46, 48, and/or 50 by software; hardware; firmware; some combination of software, hardware, and/or firmware; and/or other mechanisms for configuring processing capabilities on processor 40.

It should be appreciated that although components 42, 44, 46, 48, and 50 are illustrated in FIG. 1 as being co-located within a single processing unit, in implementations in which processor 40 comprises multiple processing units, one or more of components 42, 44, 46, 48, and/or 50 may be located remotely from the other components (e.g., such as within processor 18 of first device 12, within a server that is part of external resources 60, etc.). The description of the functionality provided by the different components 42, 44, 46, 48, and/or 50 described herein is for illustrative purposes, and is not intended to be limiting, as any of components 42, 44, 46, 48, and/or 50 may provide more or less functionality than is described. For example, one or more of components 42, 44, 46, 48, and/or 50 may be eliminated, and some or all of its functionality may be provided by other components 42, 44, 46, 48, and/or 50. As another example, processor 40 may be configured to execute one or more additional components that may perform some or all of the functionality attributed below to one of components 42, 44, 46, 48, and/or 50. In some implementations, one or more of components 42, 44, 46, 48, and/or 50 may be executed by a processor incorporated in first device 12, external resources 60, and/or other components of system 10.

Location component 42 may be configured to obtain information related to a desired physical, geographic surf location of the user. In some implementations, the information related to the desired surf location may be entered and/or selected by the user via user interface 14 of first device 12, user interface 32 of second device 30, and/or other devices. In some implementations, the desired surf location may be obtained and/or determined based on output signals from one or more sensors 22 included in first device 12, one or more sensors 36 included in second device 30, and/or other electronic signals that indicate a user's physical geographic location. In some implementations, the desired surf location may be a known surf location that is geographically close to the user's physical geographic location. In some implementations, location component 42 may be configured to cause user interface 32, user interface 14, and/or other user interfaces to present a list of nearby surf locations to the user to facilitate entry and/or selection of a desired surf location from the list by the user. In some implementations, location component 42 may be configured to designate a desired surf location entered and/or selected by a user as a user's Home Break. A user's Home Break may be displayed on a main screen of the watch (for example), and be first in all lists of spots in the app and on the watch. A user's home break may also be stored in an electronic user profile and/or be visible to a user's accepted social network within the app environment.

Surf information component 44 may be configured to obtain surf information for the desired surf location of the user. The surf information for the desired surf location of the user may be regularly obtained from one or more external sources of information (e.g., external resources 60), and/or other sources. The external sources of information may include one or more remotely located server computers (e.g., as described herein); oceanic, atmospheric, and/or other sensors; oceanic, atmospheric, and/or other information databases; and/or other external sources of information. In some implementations, a server computer associated with system 10 may obtain information from the oceanic, atmospheric, and/or other sensors; other external servers not associated with system 10; and/or other sources, and then provide the information to surf information component 44. The surf information may include (as described above) the date, the time, the surf break name, the wave height, the surf condition rating, the current tide indication, the water temperature, the alert indicator, the tide graph, the air temperature, the surf forecast, the weather information, a Bluetooth connectivity indicator, surf session physical activity tracking information (e.g., wave count, session duration, paddle count, etc.), sunrise/sunset information, wind speed, wind direction, water temperature, ocean swell direction, ocean swell height, crowd sourced "social" data related to any of the above, conditions from the past for all of above mentioned, and/or other information.

The external sources of information may be regularly accessed by surf information component 44 via a wireless communication network (e.g., the internet, a cellular communication network, etc.) such that the obtained surf information reflects substantially current surf information for the desired surf location of the user. As described above, substantially current information may include the most recent information received, stored, transmitted, etc. by the external sources of information. For example, substantially current information may include information received by a server from an oceanic sensor that reflects current oceanic conditions (e.g., real world observable conditions) conveyed by the sensor output signals. Regularly accessing the external sources of surf information may include accessing the external sources of information at regular time intervals, accessing according to a predetermined schedule, accessing external sources of information in a particular order, and/or other accessing methods that produce substantially current surf information (e.g., as opposed to months old pre-determined tide chart data), and/or information pushed to system 10 from the source as data becomes available. For example, surf information component 44 may cycle through a list of surf locations in a specified order once every 15 minutes (this is not intended to be limiting) obtaining updated surf information for an individual surf location once per cycle. Surf information and/or other current information may be manually triggered by the user such that system 10 checks to see whether a new API is available, and, if so, pull it and update information for the user immediately. In some implementations, with little and/or no action from the user, individual spots (e.g., each and every spot) in the API may be checked one by one, substantially continuously, for an update. By way of non-limiting example, a full cycle of 2989 locations/spots in the API cycles through (are checked) in approximately 500 seconds. This is not intended to be limiting and is subject to change as new spots are added and/or as server performance increases, for example.

Communication component 46 may be configured to wirelessly communicate the obtained surf information to first device 12. Communication component 46 may be configured to wirelessly communicate the obtained surf information to first device 12 responsive to first device 12 being in proximity to second device 30 to facilitate communication between first device 12 and second device 30. In some implementations, being in proximity may include being within a distance of about 20 meters or less from each other. In some implementations, being in proximity may include being within a distance of about 10 meters or less from each other. In some implementations, being in proximity may include being within a distance of about 5 meters or less from each other.

Display component 48 may be configured to cause user interface 14 of first device 12 to display the communicated surf information to the user. Causing user interface 14 to display the communicated surf information may include effectuating the presentation of the graphical user interface to the user via user interface 14. As described herein (e.g., FIG. 3A-FIG. 3E), the graphical user interface may include one or more views that include one or more fields configured to display the different types of surf information to the user (described above).

Activity tracking component 50 may be configured to track physical surfing activity of the user. Responsive to the user completing a current surf session, activity tracking component 50 may obtain information related to the physical surfing activity of the user during the current surf session (e.g., from the output signals of sensor 22 in first device 12, from information stored in electronic storage 16, and/or from other sources). Activity tracking component 50 may be configured to obtain the information related to the physical surfing activity of the user during the current surf session responsive to the user completing the current surf session and first device 12 being in proximity to second device 30 to facilitate communication between first device 12 and second device 30. Activity tracking component 50 may determine one or more current surf parameters for the current surf session based on the obtained information and/or other information. The current surf parameters may indicate an amount of physical surfing activity of the user during the current surf session and/or other information. Current surf parameters may include, for example, a paddle count, a session duration, a wave count, individual wave ratings, an overall session rating, speed of a surfer, a top speed reached, a distance surfed, a distance paddled, an aerial maneuver height of a surfer, g-forces sustained, time surfing a wave, time paddling, and/or other parameters. Activity tracking component 50 may facilitate electronic storage (e.g., in electronic storage 34, on a server that is part of external resources 60, etc.) of the current surf parameters with corresponding previous surf parameters determined for previous surf sessions to facilitate tracking the user's individual surfing activity for multiple surf sessions.

Gathering the metrics mentioned herein, as well as a recording of current surf conditions (e.g., sensors generating output signals, gathering data from external resources), may be initiated by user entering and/or selecting a "SESSIONS" (for example) mode of system 10 via the graphical user interface on the user's watch (e.g., first device 12) and/or the user's phone (e.g., second device 30) and starting a session. In some implementations, this may be initiated from the watch (for example), and may be done independent of the phone. A user may store up to 10 (for example) different sessions on the watch. Then, when within range of the phone, the user may be prompted by system 10 that they have saved sessions, and be asked if they want to sync them. The session data may be transferred from the watch to the phone and saved. The user may then see a summary of the metrics and/or the conditions for the surf session, verify the location of the surf session, add any notes or images, and then save the information to a Surf Journal associated with the user and/or save the information in other electronic locations. The user may make such a journal entry private and/or public, so that others may or may not see it. A user may create a custom alert based on any saved session in the journal, they may post an image generated by the app that summarizes their session with a background image to their social network such as Instagram, etc., and/or perform other actions based on the information in the journal and/or other information.

Responsive to receiving a positive enjoyment level rating from the user (e.g., via user interface 32 described above) for the current surf session, activity tracking component 50 may be configured to cause user interface 14 of first device 12 to display an alert to the user when subsequently obtained surf information for the surf location of the current surf session from the one or more external sources of information is substantially similar to the surf information for the current surf session. In other words, activity tracking component 50 is configured to monitor the surf conditions at the surf spot relative to how the conditions were for the highly rated surf session and then notify the user when similar good surfing conditions are present at the surf spot. In addition, system 10 may be configured such that a user may manually create alerts based on any surf conditions.

External resources 60 may include sources of information (e.g., oceanic and/or atmospheric information databases), one or more servers, a network (e.g., the internet, a cellular network), electronic storage, data entry devices, sensors, computing devices associated with individual users, and/or other resources. In some implementations, some or all of the functionality attributed herein to external resources 60 may be provided by resources included in system 10. External resources 60 may be configured to communicate with second device 30, first device 12, and/or other components of system 10 via wired and/or wireless connections, via a network (e.g., a cellular network, a local area network, and/or the internet), via Wi-Fi technology, and/or via other resources. For example, a server that is part of external resources 60 may communicate surf information to second device 30 via the internet and/or a cellular communication network. In some implementations, electronic resources 60 may include at least one server computer associated with system 10 configured to obtain information from oceanic, atmospheric, and/or other sensors; other external servers not associated with system 10; and/or other sources and provide the information to surf information component 44 of processor 40 (e.g., as shown in FIG. 2).

Figure 5:
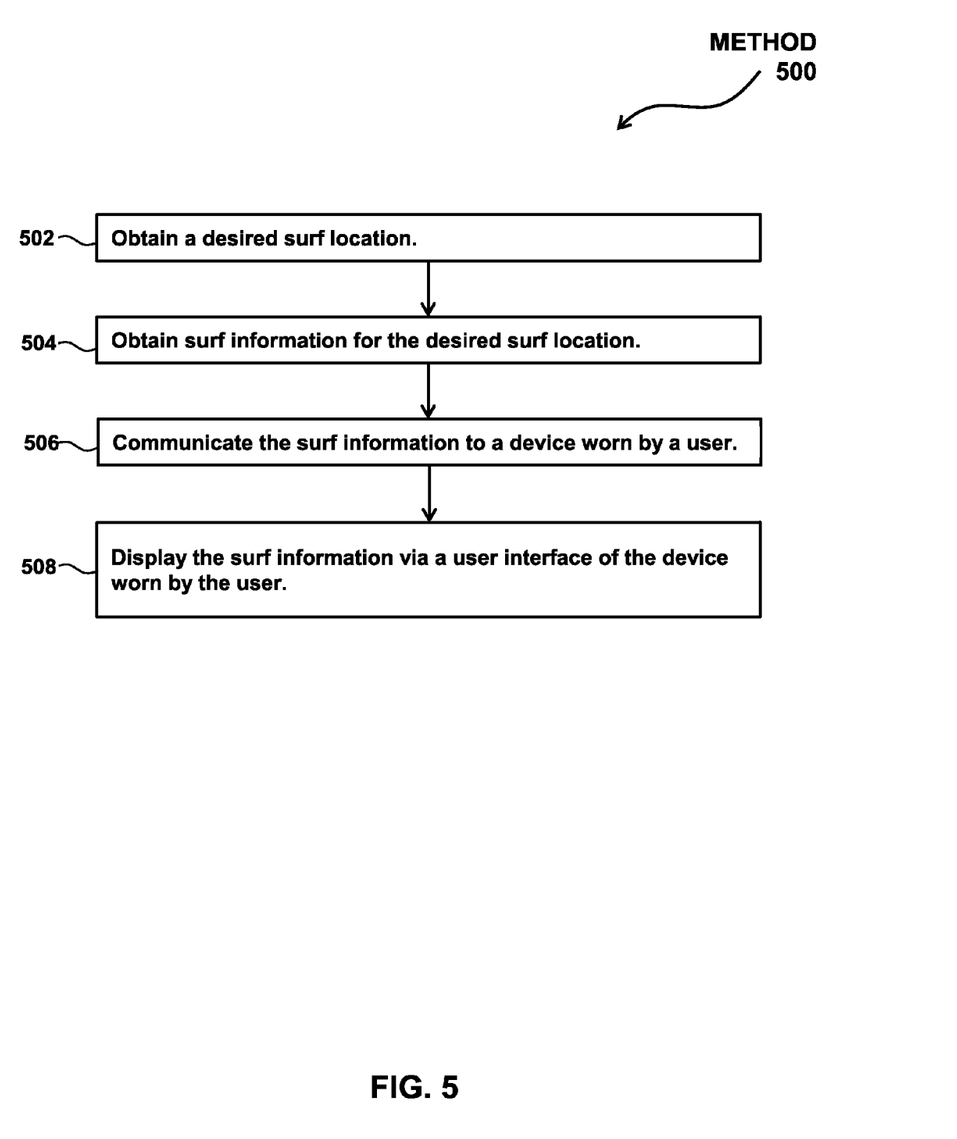
FIG. 5 illustrates a method for displaying surf information to a user via a user interface carried by a first device worn by the user.

FIG. 5 illustrates a method 500 for displaying surf information to a user via a user interface carried by a first device (e.g., a watch) worn by the user. The operations of method 500 presented below are intended to be illustrative. In some implementations, method 500 may be accomplished with one or more additional operations not described, and/or without one or more of the operations discussed. Additionally, the order in which the operations of method 500 are respectively illustrated in FIG. 5 and described below is not intended to be limiting.

In some implementations, method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 502, a desired surf location of the user may be obtained. The desired surf location may be a physical, geographic surf location of the user. The desired surf location may be obtained with a second device (e.g., a smartphone). The second device may be physically separate and unconnected from the first device and associated with the user. For example, the desired surf location may be entered and/or selected by the user via a user interface of the first device and/or the second device, the desired surf location may be obtained and/or determined based on output signals from one or more sensors included in the first device and/or the second device that indicate a user's location, and/or the desired surf location may be obtained and/or determined in other ways and/or based on other information. Operation 502 may be performed by a computer processor component that is the same as or similar to location component 42 (shown in FIG. 1 and described herein).

At an operation 504, surf information for the desired surf location may be obtained. The surf information for the desired surf location may be regularly obtained by the second device from one or more external sources of information accessed via a wireless communication network such that the obtained surf information reflects substantially current surf information for the desired surf location of the user. In some implementations, the surf information for the desired surf location of the user may be regularly obtained from one or more remote server computers accessed via a wireless communication network. The surf information may include one or more of a date, a time, a surf break name, a wave height, a surf condition rating, a current tide indication, a water temperature, an alert indicator, a tide graph, an air temperature, a surf forecast, weather information, and/or other information. Operation 504 may be performed by a computer processor component that is the same as or similar to surf information component 44 (shown in FIG. 1 and described herein).

At an operation 506, the obtained surf information may be communicated to the first device worn by the user. The obtained surf information may be communicated to the first device responsive to the first device being in proximity to the second device to facilitate communication between the first device and the second device. Operation 506 may be performed by a computer processor component that is the same as or similar to communication component 46 (shown in FIG. 1 and described herein).

At an operation 508, the communicated surf information may be displayed to the user via a user interface of the first device worn by the user. In some implementations, the user interface carried by the first device may comprise one or more views that include one or more fields for displaying one or more of the date, the time, the surf break name, the wave height, the surf condition rating, the current tide indication, the water temperature, the alert indicator, the tide graph, the air temperature, the surf forecast, the weather information, and/or other information. Operation 508 may be performed by a computer processor component that is the same as or similar to display component 48 (shown in FIG. 1 and described herein).

Figure 6:
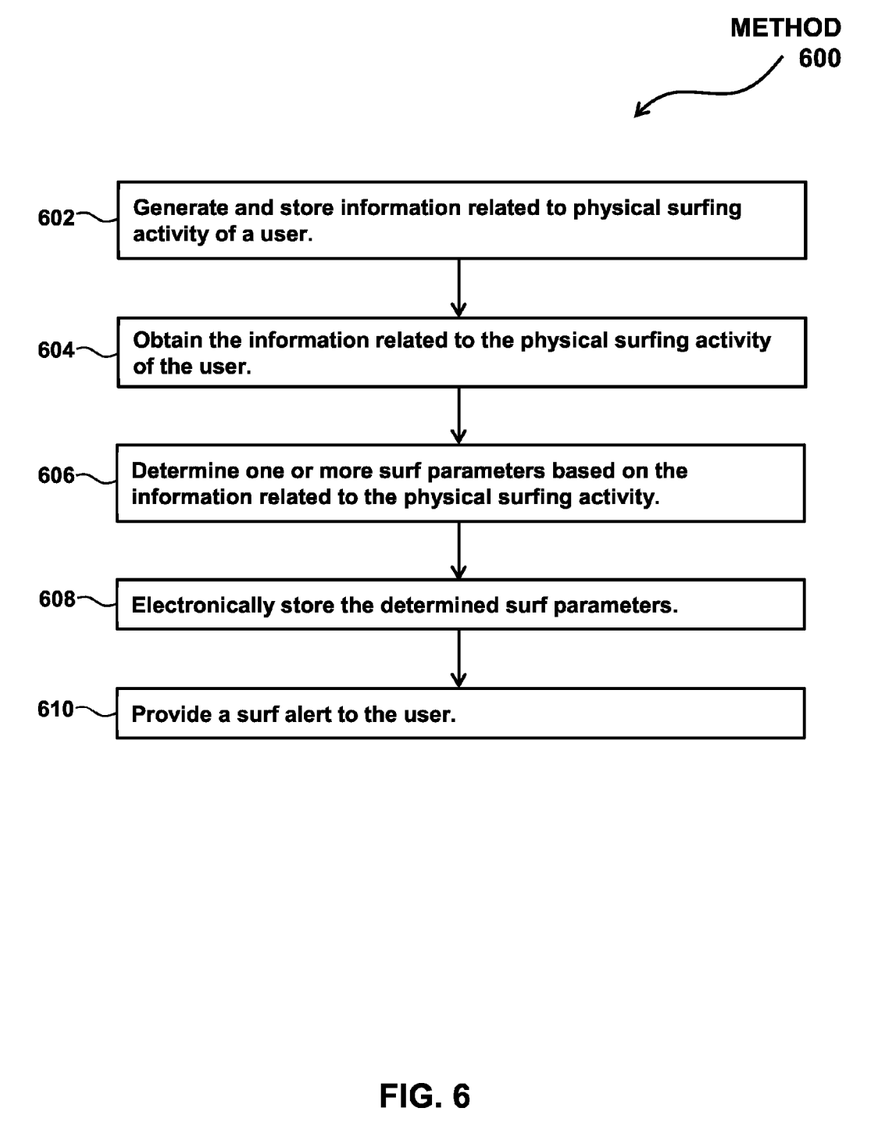
FIG. 6 illustrates a method for tracking physical surfing activity of a user.

FIG. 6 illustrates a method 600 for tracking physical surfing activity of a user. The operations of method 600 presented below are intended to be illustrative. In some implementations, method 600 may be accomplished with one or more additional operations not described, and/or without one or more of the operations discussed. Additionally, the order in which the operations of method 600 are respectively illustrated in FIG. 6 and described below is not intended to be limiting.

In some implementations, method 600 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 600 in response to instructions stored electronically on an electronic storage medium. The one or more processing devices may include one or more devices configured through hardware, firmware, and/or software to be specifically designed for execution of one or more of the operations of method 600.

At an operation 602, information related to physical surfing activity of a user may be generated and stored. The information related to physical surfing activity may be generated by one or more sensors included in the first device worn by the user. The one or more sensors may be configured to generate output signals conveying information related to the physical surfing activity of a user during a current surf session, for example. In some implementations, the one or more sensors may include one or more of a GPS sensor, a gyroscope, an accelerometer, an altimeter, a temperature sensor, and/or other sensors. The information related to the physical surfing activity of the user may be stored by electronic storage included in the first device. In some implementations, the first device may be a watch worn by the user. Operation 602 may be performed by a first device that is the same as or similar to first device 12 (shown in FIG. 1 and described herein).

At an operation 604, the information related to the physical surfing activity of the user may be obtained by a second device. The second device may be associated with the user and be physically separate and unconnected from the first device. The second device may be a smartphone, for example. The second device may be configured to obtain the information related to the physical surfing activity of the user during the current surf session from the first device responsive to the user completing the current surf session. In some implementations, the second device may be configured to obtain the information related to the physical surfing activity of the user during the current surf session responsive to the user completing the current surf session and the first device being in proximity to the second device to facilitate communication between the first device and the second device. Operation 604 may be performed by a second device that is the same as or similar to second device 30 (shown in FIG. 1 and described herein).

At an operation 606, one or more surf parameters may be determined based on the information related to the physical surfing activity. The determined surf parameters may be current surf parameters for the current surf session. The current surf parameters may indicate an amount of physical surfing activity of the user during the current surf session. For example, the current surf parameters may include one or more of a paddle count, session duration, a wave count, individual wave ratings, an overall session rating, and/or other surf parameters. Operation 606 may be performed by a second device that is the same as or similar to second device 30 (shown in FIG. 1 and described herein).

At an operation 608, the determined surf parameters may be electronically stored. The current surf parameters may be electronically stored with corresponding previous surf parameters determined for previous surf sessions to facilitate tracking the user's individual surfing activity for multiple surf sessions. In some implementations, the current surf parameters may be electronically stored with the corresponding previous surf parameters on a remotely located server. Operation 608 may be performed by a second device that is the same as or similar to second device 30 (shown in FIG. 1 and described herein).

At an operation 610, a surf alert may be provided to the user. Providing a surf alert may include receiving a surf session rating from the user that indicates an enjoyment level of the user for the current surf session; obtaining surf information for a physical, geographic surf location of the current surf session, wherein the surf information for the surf location is regularly obtained from one or more external sources of information accessed via a wireless communication network such that the obtained surf information reflects surf information for the surf location during the current surf session; and, responsive to receiving a positive enjoyment level rating from the user, causing a user interface of the first device to display an alert to the user when subsequently obtained surf information for the surf location from the one or more external sources of information is substantially similar to the surf information for the current surf session. The surf information may include one or more of a time of day, a wave height, a surf condition rating, a current tide indication, a water temperature, an air temperature, swell information, weather information, and/or other information. Operation 610 may be performed by a second device that is the same as or similar to second device 30 (shown in FIG. 1 and described herein).

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A system configured to track physical surfing activity of a user, the system comprising:
   a first device worn by the user configured to generate and store information related to physical surfing activity of a user during a current surf session, the first device comprising:

one or more sensors configured to generate output signals conveying information related to the physical surfing activity of the user during the current surf session; and electronic storage configured to electronically store the information related to the physical surfing activity of the user during the current surf session, wherein the first device is configured to communicate with a second device associated with the user that is physically separate and unconnected from the first device, the second device comprising one or more physical computer processors configured to:

responsive to the user completing the current surf session, obtain the information related to the physical surfing activity of the user during the current surf session;

determine one or more current surf parameters for the current surf session, the current surf parameters indicating an amount of physical surfing activity of the user during the current surf session; and electronically store the current surf parameters with corresponding previous surf parameters determined for previous surf sessions to facilitate tracking the user's individual surfing activity for multiple surf sessions.

2. The system of claim 1, wherein the one or more physical computer processors of the second device are configured to electronically store the current surf parameters with the corresponding previous surf parameters on a remotely located server.

3. The system of claim 1, wherein the one or more physical computer processors of the second device are configured such that the surf parameters include one or more of a paddle count, a session duration, a wave count, individual wave ratings, or an overall session rating.

4. The system of claim 1, wherein the first device is configured such that the one or more sensors include one or more of a GPS sensor, a gyroscope, an accelerometer, an altimeter, or a temperature sensor.

5. The system of claim 1, wherein the first device is a watch.

6. The system of claim 1, wherein the second device is a smartphone associated with the user.

7. The system of claim 1, wherein the one or more physical computer processors of the second device are configured to obtain the information related to the physical surfing activity of the user during the current surf session responsive to the user completing the current surf session and the first device being in proximity to the second device to facilitate communication between the first device and the second device.

8. The system of claim 1, wherein the one or more physical computer processors of the second device are further configured to:

receive a surf session rating from the user that indicates an enjoyment level of the user for the current surf session;

obtain surf information for a physical, geographic surf location of the current surf session, wherein the surf information for the surf location is regularly obtained from one or more external sources of information accessed via a wireless communication network such that the obtained surf information reflects surf information for the surf location during the current surf session; and responsive to receiving a positive enjoyment level rating from the user, cause a user interface of the first device to display an alert to the user when subsequently obtained surf information for the surf location from the one or more external sources of information is substantially similar to the surf information for the current surf session.

9. The system of claim 8, wherein the one or more physical computer processors of the second device are configured such that the surf information includes one or more of a time of day, a wave height, a surf condition rating, a current tide indication, a water temperature, an air temperature, swell information, or weather information.

* * * * *